(12) United States Patent
Robert

(10) Patent No.: US 6,517,820 B1
(45) Date of Patent: *Feb. 11, 2003

(54) COSMETIC COMPOSITION IN THE FORM OF A POWDER COMPRISING A SPECIFIC ESTER

(75) Inventor: Valérie Robert, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/518,136

(22) Filed: Mar. 3, 2000

(30) Foreign Application Priority Data

Mar. 4, 1999 (FR) .............................. 99 02705

(51) Int. Cl.⁷ ................................ A61K 7/035
(52) U.S. Cl. ........................ 424/69; 424/63; 424/64; 424/401; 424/489; 424/502; 514/844
(58) Field of Search .................... 424/401, 69, 489, 424/502, 64; 514/844

(56) References Cited

U.S. PATENT DOCUMENTS

| 5,763,497 | A | * | 6/1998 | Ikeda et al. ............. | 514/943 |
| 5,928,652 | A |   | 7/1999 | Bodelin-LeComte ....... | 424/400 |

FOREIGN PATENT DOCUMENTS

| EP | 0 001 471 | 4/1979 |
| EP | 0 132 631 | 2/1985 |
| EP | 0 194 887 | 9/1986 |
| EP | 0 651 990 | 5/1995 |
| EP | 0 792 633 | 9/1997 |
| GB | 1 357 731 | 6/1974 |
| JP | 334309 | * 11/1992 |
| WO | WO 94/21223 | 9/1994 |
| WO | WO 95/25503 | 9/1995 |

OTHER PUBLICATIONS

Derwent Publications Ltd., London, GB; AN 1991–196389, XP–002123433 (JP 03 120207), May 22, 1991.
English language Derwent Abstract of EP 0 651 990.

* cited by examiner

Primary Examiner—Thurman K. Page
Assistant Examiner—Lakshmi S. Channavajjala
(74) Attorney, Agent, or Firm—Finnegan, Henderson, Farabow, Garrett & Dunner, LLP

(57) ABSTRACT

The present invention relates to a cosmetic composition in the form of a powder containing a particulate phase and a fatty phase, characterized in that the fatty phase contains at least one fatty acid ester or at least one fatty alcohol ester, the carbonaceous chain of the fatty acid or alcohol being branched and saturated, and containing 24 to 28 carbon atoms. It also relates to the cosmetic applications of such a composition.

42 Claims, No Drawings

COSMETIC COMPOSITION IN THE FORM OF A POWDER COMPRISING A SPECIFIC ESTER

The present invention is directed to a cosmetic composition in the form of a powder, for example a loose, compacted, pressed or cast powder, comprising at least one specific ester.

It is known to use in a formulation of make-up powders containing, on the one hand, a particulate phase comprising in particular pigments and fillers and, on the other hand, as a binder a fatty phase comprising fatty substances. The fatty phase is intended to confer a degree of density on the finished product, to give softness and an emollient property to the make-up product and to promote its adhesion to the skin.

The formulation of binding agents in powders, in particular in compact powders, raises numerous difficulties. These difficulties result because the final composition must be sufficiently homogeneous and compact to exhibit good suitability for removal and to avoid fragmentation caused in particular by impacts.

It is possible to use, as a binder, a mixture of mineral and vegetable oils in combination with esters. However, the products comprising these esters can result in products which lack softness and can even result in poor dispersion of the pigmentary phase.

It is also possible to use silicone oils, which can contribute slip, softness and ease of spreading. However, the properties of hold of the make-up and of impact strength in the products using silicone oils are mediocre.

Finally, some perfluorinated oils, in particular perfluoropolyethers, are well known as contributing softness to cosmetic compositions. In such a composition, however, the formulator is then confronted with problems of insolubility of these oils in conventional hydrocarbonaceous oils or in silicone oils. This insolubility results in the comprising perfluorinated oils exhibit mediocre properties of impact strength. Some of these oils can also exhibit the disadvantage of a poor dispersion of the pigmentary phase. In such a poor dispersion, the color contributed by the pigment is relatively low in intensity and this can bring about a "white effect", which is undesirable, aesthetically speaking.

Furthermore, it happens that compositions in the form of a powder are subject to the phenomenon of migration. This is because it has been found that some compositions have a tendency to spread inside the fine lines and/or wrinkles of the skin, in the case of face powders, or into the folds of the eyelid, in the case of eyeshadows. There has also been observed, in the case in particular of eyeshadows, the appearance of streaks in the make-up generated by the movements of the eyelids. Such compositions exhibit an unsatisfactory hold.

All these phenomena result in an unsightly effect which it is clearly desirable to avoid.

The inventors have found, unexpectedly, that the use as a powder binder of at least one specific oily ester, which ester is composed of saturated and branched ($C_{24}$ to $C_{28}$) fatty acids or fatty alcohols, makes it possible to obtain a powder which not only exhibits excellent cosmetic properties but which furthermore exhibits an improved hold.

The present invention is therefore directed to a cosmetic composition in the form of a powder comprising a particulate phase and a fatty phase, characterized in that the fatty phase comprises at least one fatty acid ester or fatty alcohol ester, the carbonaceous chain of the fatty acid or alcohol being saturated and branched, and comprising 24 to 28 carbon atoms.

The compositions in the form of a powder thus obtained exhibit an excellent hold. They do not transfer and do not migrate into the folds of the skin. They also exhibit an excellent dispersion of the pigments. The composition obtained is very homogeneous and it remains homogenous even after application to the skin, this being the case for several hours.

The compositions according to the invention also exhibit excellent cosmetic properties: they adhere sufficiently to the skin but not too much; they are very soft; and they are easily applied.

Furthermore, these compositions are easy to compact, they readily disintegrate, and they exhibit good hardness. In particular, they exhibit good cohesion of the product in the dish while allowing satisfactory disintegration of the product. In the case of compacted powders, for example, they exhibit outstanding strength when dropped and the percentage of loss of product after being dropped is very low.

In another embodiment, the present invention is directed to a cosmetic process for making up or caring for the skin, in particular of the body, or mucous membranes (interior of the lower eyelids) of human beings comprising the application, to the skin, body or mucous membranes, of the composition as defined above.

In a further embodiment, the present invention is directed to the use of at least one fatty acid ester or fatty alcohol ester, the carbonaceous chain of the fatty acid or alcohol being saturated and branched, and comprising 24 to 28 carbon atoms, in a cosmetic composition in the form of a powder with the aim of improving the hold on the skin of the composition.

In yet another embodiment, the invention is directed to the use of at least one fatty acid ester or fatty alcohol ester, the carbonaceous chain of the fatty acid or alcohol being saturated and branched, and comprising 24 to 28 carbon atoms, in the preparation of a composition in the form of a powder with the aim of improving the hold on the skin of the composition.

In another embodiment, the present invention is directed to the use of at least one fatty acid ester or fatty alcohol ester, the carbonaceous chain of the fatty acid or alcohol being saturated and branched, and comprising 24 to 28 carbon atoms, in a composition in the form of a powder, especially cosmetic and more particularly compact, with the aim of improving the impact strength of the composition.

The compositions according to the invention especially find a particularly advantageous application in the field of making up and/or caring for the skin and mucous membranes. The term "mucous membrane" is understood by those of ordinary skill in the art, and includes, in particular the interior part of the lower eyelid. Thus, the invention finds a very specific application in the field of products for making up the face and the skin, such as eyeshadows, face and body powders, foundations, concealers or make-up products for the body.

Other characteristics, aspects and advantages of the present invention will become apparent on reading the detailed description which will follow.

The compositions of the invention are cosmetic powders. They generally comprise at least 70% by weight, preferably from 77 to 99.9% by weight, with respect to the total weight of the composition, of particulate or pulverulent phase.

The compositions of the invention also comprise as a binder a fatty phase comprising fatty substances which facilitate the adhesion to the skin of the pulverulent compounds and their cohesion to each other in the final composition. This fatty phase can represent up to 30% by weight, preferably from 0.1 to 23% by weight and more preferably from 3 to 20% by weight with respect to the total weight of the composition.

The fatty phase of the compositions according to the invention comprises at least one fatty acid ester or fatty alcohol ester, the carbonaceous chain of the fatty acid or alcohol being saturated and branched and comprising 24 to 28 carbon atoms. The word ester, according to the invention, means a monoester or a polyester. The term "polyester" is understood to mean, within the meaning of the present invention, a compound comprising more than one ester functional group, such as, for example, diesters, triesters, tetraesters and the like. The ester according to the invention is preferably chosen from polyesters. The ester according to the invention preferably comprises at least 2 branched ($C_{24}$ to $C_{28}$) chains. The word branched means at least one pendant hydrocarbonaceous chain comprising in particular from 1 to 14 carbon atoms.

The ester of the invention therefore comprises a saturated ($C_{24}$ to $C_{28}$) fatty alcohol or fatty acid residue, in particular a Guerbet fatty alcohol of following formula (a) or a Guerbet fatty acid of following formula (b) respectively:

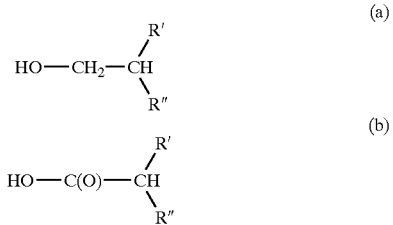

in which R' and R", which are identical or different, are chosen from saturated alkyl radicals, the sum of the carbon atoms of which ranges from 22 to 26. The R" alkyl radical preferably comprises two carbon atoms less than the R' alkyl radical.

The ester of the composition of the invention is preferably an oily ester which is liquid at room temperature (approximately 25° C.) exhibiting a high molecular weight, that is to say having a carbon number of greater than or equal to 50 and in particular of greater than or equal to 70. The advantage of a product which is liquid at room temperature in comparison with a product which is pasty or solid at room temperature lies in the greater number of its applications and its ease of use. Furthermore, the fact that this ester exhibits a high molecular weight makes it possible to obtain film-forming compositions which are persistent in water, which is widely desired for protection products, in particular sun protection products. This ester exhibits, inter alia, a refractive index of greater than 1.45 at 20° C. and an iodine number$\leq$4.

This ester, despite its high molecular weight, is neither greasy nor heavy nor sticky and confers, on the composition comprising it, notable comfort properties.

The ester according to the invention is advantageously an ester of a branched ($C_{24}$–$C_{28}$) fatty acid, such as 2-decyltetradecanoic acid, and more specifically an ester of a polyol, such as glycerol, which can be a mono-, di- or triglyceride. This ester is preferably a triglyceride of branched ($C_{24}$–$C_{28}$) fatty acids of the Guerbet type and in particular a triglyceride of a ($C_{24}$) fatty acid, such as 2-decyl-tetradecanoic acid.

Preferably, at least one of the branched chains of the ester comprises 24 carbon atoms. More preferably, the ester according to the invention is chosen from triglycerides of a branched ($C_{24}$) fatty acid, pentaerythritol esters of a branched ($C_{24}$) fatty acid, esters of a branched ($C_{24}$) fatty alcohol and of diacids, and their mixtures.

A preferred triglyceride is, for example, glyceryl tri(2-decyltetradecanoate), sold under the reference DUB TGI 24 by the company Stearinerie Dubois. This ester exhibits a saponification number of 140 to 150, a refractive index>1.45 and in particular ranging from 1.454 to 1.459 at 20° C., an iodine number$\leq$4, a hydroxyl number$\leq$30 and an acid number$\leq$10. Its carbon number is 75.

Use may also be made of pentaerythritol esters of a ($C_{24}$) fatty acid, such as pentaerythrityl tetra(2-decyltetradecanoate) (with 101 carbon atoms), sold under the reference DUB PTI 24 by the company Stearinerie Dubois.

When the alcohol combined with the branched ($C_{24}$ to $C_{28}$) fatty acid is a polyol, the esterification can be partial and can then relate to 1, 2, 3 or more OH groups, depending on the alcohol used, or can be total.

Mention may be made of an ester of the invention comprising a fatty alcohol residue with a saturated branched ($C_{24}$ to $C_{28}$) chain, of di(decyltetradecyl) dimerates (with 84 carbon atoms), such as that sold under the reference DUB DI 24D by the company Stéarinerie Dubois, or decyltetradecyl neopentanoate (with 29 carbon atoms) or decyltetradecyl isostearate, sold by the company CONDEA under the reference Isofol Ester 2482 (with 42 carbon atoms). Dimerates are esters resulting from diacids, the latter generally being obtained from an unsaturated ($C_6$ to $C_{24}$) acid, such as oleic acid, linoleic acid, linolenic acid and the like.

The ester according to the invention preferably does not exhibit surfactant properties.

The ester of the invention can represent up to 100% by weight of the fatty phase of the composition according to the invention. The ester can thus be present in the composition according to the invention at a content ranging up to 30% by weight with respect to the total weight of the composition. The ester according to the invention is preferably present at a content ranging from 0.1 to 23% of the weight of the composition, more preferably from 2 to 20%, and generally in an amount sufficient to confer, on the composition, properties of good cohesion and of improved hold.

In addition to the above specific ester, the fatty phase of the composition according to the invention can comprise any other fatty substance, such as oils, waxes and/or pasty fatty compounds.

Pasty fatty compounds can be defined using at least one of the following physicochemical properties:
  a viscosity of 0.1 to 40 Pa·s (1 to 400 poises), preferably 0.5 to 25 Pa·s, measured at 40° C. with a Contraves TV rotary viscometer equipped with an MS-r3 or MS-r4 rotor at a frequency of 60 Hz,
  a melting point of 25–70° C., preferably 25–55° C.

The fatty substances can be chosen from oils and/or waxes of mineral, animal or vegetable origin, fluorinated oils, fatty acid esters and/or their mixtures.

Mention may be made, among the oils which can be used, of mink oil, turtle oil, soybean oil, grape seed oil, sesame oil, maize oil, rapeseed oil, sunflower oil, cottonseed oil, avocado oil, olive oil, castor oil, jojoba oil or groundnut oil; hydrocarbon oils, such as liquid paraffins, squalane or liquid petrolatum; fatty esters, such as isopropyl myristate, isopropyl palmitate, butyl stearate, hexyl laurate, isononyl isononate, 2-ethylhexyl palmitate, 2-hexyldecyl laurate, 2-octyldecyl palmitate, 2-octyldodecyl myristate or lactate, di(2-ethylhexyl) succinate, diisostearyl malate, or glyceryl or diglyceryl triisostearate; perfluorinated oils; higher fatty acids, such as myristic acid, palmitic acid, stearic acid, behenic acid, oleic acid, linoleic acid, linolenic acid or isostearic acid; higher fatty alcohols, such as cetanol, stearyl alcohol or oleyl alcohol, and/or their mixtures.

Mention may be made, among the waxes which can be used, of beeswaxes, lanolin waxes and Chinese insect waxes; carnauba, candelilla or ouricury waxes, cork fibre waxes, sugar cane waxes, Japan waxes, hydrogenated jojoba waxes and hydrogenated oils, such as hydrogenated sunflower oil, hydrogenated castor oil, hydrogenated coconut oil and hydrogenated lanolin; paraffin waxes, microcrystalline waxes, montan waxes and ozokerites; polyethylene waxes, waxes obtained by the Fisher-Tropsch synthesis, waxy copolymers and their esters; and silicone waxes, such as polyalkoxy- and polyalkylsiloxanes, and/or their mixtures.

The fatty phase of the compositions according to the invention can optionally comprise a volatile part, such as, for example, volatile oils.

The term "volatile oil" is understood to mean any compound capable of evaporating on contact with the skin. Use is preferably made of oils with a flash point sufficiently high to allow the use of these oils in formulation and sufficiently low to produce the desired evanescent effect. Oils with a flash point of the order of 40–100° C. are preferably employed.

These volatile compounds can be chosen in particular from hydrocarbonaceous oils, such as isoparaffins and in particular isododecane.

The fatty phase can additionally comprise additives, such as lipophilic cosmetic active principles and/or fat-soluble ingredients generally used in cosmetics, such as fragrances or sunscreens. These additives can preferably be present in a proportion ranging from 20 to 70% by weight with respect to the total weight of the fatty phase.

The compositions according to the invention can also comprise silicone resins comprising a combination of the $R_3SiO_{1/2}$, $R_2SiO_{2/2}$, $RSiO_{3/2}$ and $SiO_{4/2}$ units in which R is chosen from hydrogen, a ($C_1$–$C_6$) alkyl radical and a phenyl radical.

The composition of the invention can additionally comprise any additive conventionally used in the cosmetics field, such as antioxidants, essential oils, preservatives, neutralizing agents, water-in-oil or oil-in-water surfactants, vitamins or antiwrinkle active principles.

Of course, a person skilled in the art will take care to choose the optional additional compounds and/or their amounts so that the advantageous properties of the composition according to the invention are not, or not substantially, detrimentally affected by the envisaged addition.

The composition according to the invention also comprises a particulate phase which can comprise pigments, peardescent agents, fillers and/or their mixtures conventionally used in cosmetic compositions.

The term "pigments" should be understood as comprising white or colored, and inorganic or organic particles which are insoluble in the medium and which are intended to color and/or opacify the composition.

The pigments can be present in a proportion of 0–40% by weight with respect to the total weight of the composition and preferably in a proportion of 2–20%. They can be white or colored, inorganic or organic, and conventional or nanometric in size. Mention may be made, among inorganic pigments and nanopigments, of titanium, zirconium or cerium dioxides and zinc, iron or chromium oxides, titanium dioxide nanopigments, ferric blue and/or their mixtures. Mention may be made, among organic pigments, of carbon black and lakes, commonly employed to confer a make-up effect on the lips and skin, which are calcium, barium, aluminium or zirconium salts of acid dyes, such as haloacid, azo or anthraquinone dyes, and/or their mixtures.

The pigments can in particular be coated with silicone compounds, such as polydimethylsiloxanes, and/or with polymers, in particular polyethylenes. Mention may thus be made of the SA pigments from Maprecos or the P1 pigments from Myoshi.

The term "fillers" should be understood as comprising colorless or white, inorganic or synthetic, and lamellar or non-lamellar particles which are intended to give body or stiffness to the composition and/or softness, mattness and uniformity to the make-up.

The fillers, which can be present in the composition at a content ranging from 0 to 99% by weight, preferably from 0–40% by weight, with respect to the total weight of the composition, preferably 2–20%, can be inorganic or synthetic and lamellar or non-lamellar. Mention may be made of talc, mica, silica, kaolin, powders formed of Nylon, powders formed of poly-β-alanine, powders formed of polyethylene, Teflon, lauroyllysine, starch, boron nitride, bismuth oxychloride, powders formed of tetrafluoroethylene polymers, poly(methyl methacrylate) powders, polyurethane powders, polystyrene powders, polyester powders, synthetic hollow microspheres, such as EXPANCEL (Nobel Industrie), microsponges, such as POLYTRAP(Dow Corning), silicone resin microbeads (TOSPEARLS from the Company Toshiba, for example), zinc and titanium oxides, zirconium or cerium oxides, precipitated calcium carbonate, magnesium carbonate and hydrated magnesium carbonate, hydroxyapatite, hollow silica microspheres (SILICA BEADS from the Company Maprecos), glass or ceramic microcapsules, metal soaps derived from organic carboxylic acids having from 8 to 22 carbon atoms, preferably from 12 to 18 carbon atoms, for example zinc, magnesium or lithium stearate, zinc laurate or magnesium myristate, and/or their mixtures.

The term "pearlescent agents" should be understood as comprising iridescent particles which reflect the light. The pearlescent agents can be present in the composition at a content ranging from 0–60% by weight, preferably from 0–40% by weight, more preferably from 2–20% by weight, with respect to the total weight of the composition. Mention may be made, among the pearlescent agents which can be envisaged, of natural mother-of-pearl, mica covered with titanium oxide, with iron oxide, with natural pigment or with bismuth oxychloride, and colored titanium oxide-coated mica, and/or their mixtures.

In particular, by virtue of the ester according to the invention, it is possible to prepare compact powders comprising a high level of pearlescent agent. Thus, preferably, when the level of pearlescent agents in the compositions according to the invention is greater than or equal to 30% by weight with respect to the total weight of the composition, then the level of ester according to the invention is greater than or equal to 15% by weight with respect to the total weight of the composition.

The composition according to the invention can be provided in the form of a powder, for example compacted, loose, pressed or cast. In the case of a loose powder, for example, the fatty phase can represent up to 10% by weight with respect to the total weight of the composition, preferably from 1 to 5% by weight with respect to the total weight of the composition. For a compacted powder, the content of fatty phase can represent from 1 to 30% by weight, preferably from 5 to 20% by weight, with respect to the total weight of the composition. For a cast powder, the content of fatty phase can represent from 1 to 30% by weight, preferably from 5 to 20% by weight, with respect to the total weight of the composition.

According to a preferred embodiment of the invention, the composition according to the invention is a compact powder.

The compositions according to the invention are prepared according to known methods for the preparation of cosmetic powders, in particular compact powders.

The invention is illustrated in more detail in the following non-limiting examples.

In the following examples, the amounts are given as percentage by weight with respect to the total weight of the composition.

EXAMPLE 1

Comparative

The following composition A according to the invention and the following comparative composition B was prepared:

| | |
|---|---|
| Talc | q.s. for 100% |
| Mica | 20% |
| BiOCl | 10% |
| $TiO_2$ | 2% |
| Metal salt | 3% |
| Pigments | 15% |
| Nylon | 20% |
| Binder | 5.5% | with:

| Composition | Binder |
|---|---|
| Composition A (invention) | glyceryl tri(2-decyltetra-decanoate) |
| Composition B (comparative) | polydecene-glyceryl triiso-stearate |

These compositions were prepared in the following way: the pulverulent compounds were first mixed. The binder was added and mixing was again carried out. The combined mixture was sieved and then compacted in a dish.

These compositions can be provided, for example, in the form of an eyeshadow.

The comparative composition B comprised a binder according to the prior art as disclosed in EP 792,633. This binder comprised glyceryl triisostearate, which is an ester with a chemical structure similar to glyceryl tri(2-decyltetra-decanoate).

The compositions A and B were respectively applied to both eyelids of several people. The following criteria were subsequently evaluated:

the adhesion: the composition B was considered to be too adherent, the softness: ⅔ of the people found the composition A to be softer than the composition B, the ease of application: all the people found that the composition A was easier to apply than the composition B.

Overall, the composition A was considered to exhibit better cosmetic properties than the composition B.

Thus, the composition according to the invention, which comprised an ester according to the invention, namely glyceryl tri(2-decyltetradecanoate), exhibited improved cosmetic properties with respect to a composition comprising an ester, glyceryl triiso-stearate, with a similar but different chemical structure.

EXAMPLE 2

Comparative

The compositions A and B of Example 1 were respectively applied to each of the two eyelids of a panel of 6 people. 83% of these people found that:

the composition A was more intense after 4 hours, the composition A was more homogeneous after 4 hours, the composition A remained more matt after 4 hours.

17% of the people did not notice any difference between the two products.

Thus, for 83% of the people tested, the composition A according to the invention exhibited an improved hold.

EXAMPLE 3

Comparative

The impact strengths of the compositions A and B of Example 1 were compared at an equivalent hardness. This hardness was measured using a Zwick durometer graduated from 0 to 100 Shore A units. The needle of the durometer was made to penetrate close to the centre of the dish in which the product to be measured is found and the hardness was read on the graduated dial. In order to obtain an equivalent hardness for the compositions A and B, the composition A was compacted at a compacting pressure of 80 bar and the composition B was compacted at a compacting pressure of 70 bar.

Drop tests were carried out according to the following protocol: weighing was carried out on each sample compacted beforehand in a dish. Each sample was then dropped 10 times from a height of 20 cm vertically onto a sandstone slab. Each sample was again weighed and the percentage of product lost was calculated with respect to the weight; of the initial product.

The results are collated in the table below:

| Composition | % of loss of product after dropping | Hardness (° Shore) |
|---|---|---|
| Composition A (invention) | 1.5% | 59 |
| Composition B (comparative) | 2.9% | 58 |

At an equivalent hardness, corresponding to a cosmetically satisfactory level of disintegration, the composition according to the invention exhibited better results in the drop test, and therefore in impact strength, than the composition comprising an ester not in accordance with the present invention.

EXAMPLE 4

The following composition C according to the invention was prepared:

| | |
|---|---|
| Talc | q.s. for 100% |
| Mica | 10% |
| BiOCl | 3% |

-continued

| | |
|---|---|
| TiO₂ | 3% |
| Metal salt | 2% |
| Pigments | 4% |
| Nylon | 10% |
| Pearlescent agents | 50% |
| Glyceryl tri(2-decyltetradecanoate), sold under the trade name "DUB TGI 24" by the company Stéarinerie Dubois | 15.4% |

This composition was prepared according to the preparation method of Example 1. Despite the presence of 50% of pearlescent agents, it was possible to compact it. Furthermore, this composition exhibited good cohesion. For a compacting pressure of 120 bar and a hardness, measured as in Example 3, of 24 Shore A, this composition exhibited a percentage of loss of product after dropping, measured as in Example 3, of 2%, which is very low for a product comprising such a high level of pearlescent agent.

The composition D was also prepared, corresponding to the composition C in which the 15.4% of glyceryl tri(2-decyltetradecanoate) had been replaced by 15.4% of silicone. For a compacting pressure of 120 bar and a hardness equivalent to that of the composition C, the composition D exhibited a percentage of loss of product after dropping of 100%.

What is claimed is:

1. A cosmetic composition in the form of a powder comprising:
   a particulate phase and
   a fatty phase,
   wherein the fatty phase comprises at least one fatty acid ester or at least one fatty alcohol ester, the at least one fatty acid ester or the at least one fatty alcohol ester being saturated and branched, and comprising at least two carbonaceous chains comprising 24 to 28 carbon atoms, wherein the at least one fatty acid ester or at least fatty alcohol ester is a polyester.

2. The composition according claim 1, wherein the at least one fatty acid ester or the at least one fatty alcohol ester has a carbon number of greater than or equal to 50.

3. The composition according to claim 2, wherein the at least one fatty acid ester or the at least one fatty alcohol ester has a carbon number of greater than or equal to 70.

4. The composition according to claim 1, wherein at least one of the at least two branched ($C_{24}$ to $C_{28}$) chains comprises 24 carbon atoms.

5. The composition according claim 1, wherein the at least one fatty acid ester or the at least one fatty alcohol ester is chosen from triglycerides of a branched $C_{24}$ fatty acid, pentaerythritol esters of a branched $C_{24}$ fatty acid, and esters of a branched $C_{24}$ fatty alcohol and of diacids.

6. The composition according to claim 1, wherein the at least one fatty acid ester or the at least one fatty alcohol ester exhibits a refractive index of greater than 1.45 at 20° C.

7. The composition according claim 1, wherein the at least one fatty acid ester or the at least one fatty alcohol ester exhibits an iodine number of less than or equal to 4.

8. The composition according to claim 1, wherein the at least one fatty acid ester or the at least one fatty alcohol ester is glyceryl tri(2-decyltetradecanoate).

9. The composition according to claim 1, wherein the at least one fatty acid ester or the at least one fatty alcohol ester is present in the composition in an amount greater than 0 to 30% by weight with respect to the total weight of the composition.

10. The composition according to claim 9, wherein the at least one fatty acid ester or the at least one fatty alcohol ester is present in the composition in an amount from 0.1 to 23% by weight.

11. The composition according to claim 10, wherein the at least one fatty acid ester or the at least one fatty alcohol ester is present in the composition in an amount from 2 to 20% by weight, with respect to the total weight of the composition.

12. The composition according claim 1, wherein the fatty phase additionally comprises at least one fatty substance chosen from oils, waxes of mineral, animal or vegetable origin, fluorinated oils, and fatty acid esters.

13. The composition according claim 1, wherein the fatty phase additionally comprises a volatile oil.

14. The composition according to claim 1, wherein the particulate phase comprises at least one pigment chosen from inorganic pigments and nanopigments.

15. The composition according to claim 1, wherein the particulate phase comprises at least one pigment chosen from titanium dioxide, zirconium dioxide, cerium dioxide, zinc oxide, iron oxide, chromium oxide, titanium dioxide nanopigments, ferric blue, carbon black, lakes, pigments coated with silicone compounds, and pigments coated with polymers.

16. The composition according to claim 15, wherein the silicone compounds are polydimethylsiloxanes.

17. The composition according to claim 15, wherein the lakes are chosen from calcium, barium, aluminium and zirconium salts of acid dyes.

18. The composition according to claim 17, wherein the acid dyes are chosen from haloacid, azo and anthraquinone dyes.

19. The composition according to claim 15, wherein the polymers is polyethylenes.

20. The composition according to claims 14 or 15, wherein the pigments are present in the composition in an amount greater than 0 to 40% by weight relative to the total weight of the composition.

21. The composition according to claims 14 or 15, wherein the pigments are present in the composition in an amount ranging 2 to 20% by weight relative to the total weight of the composition.

22. The composition according claim 1, wherein the particulate phase comprises at least one filler chosen from talc, mica, silica, kaolin, powders formed of Nylon, powders formed of poly-β-alanine, powders formed of polyethylene, Teflon, lauroyllysine, starch, boron nitride, bismuth oxychloride, powders formed of tetrafluoroethylene polymers, poly(methyl methacrylate) powders, polyurethane powders, polystyrene powders, polyester powders, synthetic hollow microspheres, microsponges, silicone resin microbeads, zinc oxide, titanium oxide, zirconium oxide, cerium oxide, precipitated calcium carbonate, magnesium carbonate, hydrated magnesium carbonate, hydroxyapatite, hollow silica microspheres, glass microcapsules, ceramic microcapsules, and metal soaps derived from organic carboxylic acids having from 8 to 22 carbon atoms.

23. The composition according to claim 22, wherein the metal soaps derived from organic carboxylic acids have from 12 to 22 carbon atoms.

24. The composition according to claim 22, wherein the metal soaps derived from organic carboxylic acids are chosen from zinc stearate, magnesium stearate, lithium stearate, zinc laurate and magnesium myristate.

25. The composition according to claim 22, wherein the at least one filler is present in the composition in an amount greater than 0 to 99% by weight with respect to the total weight of the composition.

26. The composition according to claim 25, wherein the at least one filler is present in the composition in an amount greater than 0 to 40% by weight with respect to the total weight of the composition.

27. The composition according to claim 26, wherein the at least one filler is present in the composition in an amount ranging from 2 to 20% by weight with respect to the total weight of the composition.

28. The composition according to claim 1, wherein the particulate phase comprises at least one pearlescent agent.

29. The composition according to claim 28, wherein the at least one pearlescent agent is present in the composition in an amount greater than 0 to 60% by weight with respect to the total weight of the composition.

30. The composition according to claim 29, wherein the at least one pearlescent agent is present in the composition in an amount greater than 0 to 40% by weight with respect to the total weight of the composition.

31. The composition according to claim 28, wherein the at least one pearlescent agent is present in the composition in an amount ranging from 2 to 20% by weight with respect to the total weight of the composition.

32. The composition according to claim 1, wherein the composition in the form of a compact powder.

33. The composition according to claim 31, wherein the composition comprises a level of pearlescent agents of greater than or equal to 30% by weight with respect to the total weight of the composition and a level of ester of greater than or equal to 15% by weight with respect to the total weight of the composition.

34. The composition according to claim 1, wherein the composition is provided in the form of concealers, foundations, eyeshadows, face powders, body powders, or make-up products for the body.

35. A process for making up or caring for the skin or mucous membranes of human beings comprising applying to the skin or mucous membranes a composition in the form of a powder comprising:
   a particulate phase and
   a fatty phase,
   wherein the fatty phase comprises at least one fatty acid ester or at least one fatty alcohol ester, the fatty acid ester or the fatty alcohol ester being saturated and branched, and comprising at least two carbonaceous chains comprising 24 to 28 carbon atoms, wherein the at least one fatty acid ester or at least fatty alcohol ester is a polyester.

36. The process according to claim 35, wherein the skin is the body.

37. A process of improving the hold of a composition on skin comprising applying to the skin an effective amount of a composition comprising at least one fatty acid ester or at least one fatty alcohol ester, the at least one fatty acid ester or the at least one fatty alcohol ester being saturated and branched, and comprising at least two carbonaceous chains comprising 24 to 28 carbon atoms, wherein the at least one fatty acid ester or at least fatty alcohol ester is a polyester.

38. The process according to claim 37, wherein the composition is a compact.

39. A process for preparing a composition in the form of a powder comprising providing to the composition at least one fatty acid ester or at least one fatty alcohol ester, the fatty acid or alcohol being saturated and branched and comprising at least two carbonaceous chains comprising 24 to 28 carbon atoms, wherein the at least one fatty acid ester or at least fatty alcohol ester is a polyester, wherein the composition has improved hold on skin.

40. A process of improving impact strength of a composition in the form of a powder comprising providing to the composition an effective amount of at least one fatty acid ester or fatty alcohol ester, the at least one fatty acid ester or the fatty alcohol ester being saturated and branched, and comprising at least two carbonaceous chains comprising 24 to 28 carbon atoms, wherein the at least one fatty acid ester or at least fatty alcohol ester is a polyester.

41. The process according to claim 40, wherein the composition is a compact.

42. The composition according to claim 1, wherein the polyester is liquid at room temperature.

* * * * *

UNITED STATES PATENT AND TRADEMARK OFFICE
CERTIFICATE OF CORRECTION

PATENT NO.    : 6,517,820 B1
DATED         : February 11, 2003
INVENTOR(S)   : Valérie Robert It is certified that error appears in the above-identified patent and that said Letters Patent is hereby corrected as shown below:

Column 9,
Line 39, "least fatty" should read -- least one fatty --.
Lines 40, 49, 54 and 57, "according claim" should read -- according to claim --.

Column 10,
Lines 9, 13 and 42, "according claim" should read -- according to claim --.
Line 33, "polymers is" should read -- polymers are --.
Line 40, "ranging 2" should read -- ranging from 2 --.

Column 11,
Line 24, "composition in" should read -- composition is in --.
Line 25, "claim 31" should read -- claim 32 --.

Column 12,
Lines 6, 16 and 34, "least fatty" should read -- least one fatty --.
Lines 24-25, "least fatty" should read -- least one fatty --.

Signed and Sealed this

Twenty-second Day of April, 2003

JAMES E. ROGAN
*Director of the United States Patent and Trademark Office*